United States Patent
Mayr

(10) Patent No.: US 6,682,743 B2
(45) Date of Patent: Jan. 27, 2004

(54) ALTERED STRAIN OF THE MODIFIED VACCINIA VIRUS ANKARA (MVA)

(75) Inventor: Anton Mayr, Starnberg (DE)

(73) Assignee: Bavarian Nordic A/S, Copenhagen (DK)

( * ) Notice: Subject to any disclaimer, the term of this patent is extended or adjusted under 35 U.S.C. 154(b) by 0 days.

(21) Appl. No.: 10/204,782

(22) PCT Filed: Mar. 10, 2001

(86) PCT No.: PCT/EP01/02703

§ 371 (c)(1),
(2), (4) Date: Aug. 22, 2002

(87) PCT Pub. No.: WO01/68820

PCT Pub. Date: Sep. 20, 2001

(65) Prior Publication Data

US 2003/0013190 A1 Jan. 16, 2003

(30) Foreign Application Priority Data

Mar. 14, 2000 (DK) .......................................... 2000 00410

(51) Int. Cl.[7] .......................... A61K 39/285; C12N 7/00; C12N 7/01; C12N 15/863
(52) U.S. Cl. ................. 424/199.1; 424/232.1; 424/281.1; 424/93.2; 435/235.1; 435/237; 435/320.1; 435/69.1; 435/91.1; 435/456; 435/325
(58) Field of Search ........................... 424/199.1, 232.1, 424/281.1, 93.2, 93.6; 435/235.1, 471, 477, 237, 325, 69.1, 91.1, 456; 514/44

(56) References Cited

U.S. PATENT DOCUMENTS 5,185,146 A * 2/1993 Altenburger ................ 435/69.1

FOREIGN PATENT DOCUMENTS

| WO | WO 95/22978 | 8/1995 |
| WO | WO 97/02355 | 1/1997 |

OTHER PUBLICATIONS

Egan et al. "Evolving scientific and regulatory perspectives on cell substrates for vaccine development." Workshop, Sep. 7, 1999. http://www.fda.gov/cber/minutes/0907evolv.txt.*
Drexler et al. Journal of General Virology 79:347–352, 1998.*
"Host Range and Cytopathogenicity . . . " by M.W. Carroll et al. Virology 238, 198–211, (1997).

* cited by examiner

Primary Examiner—Mary E. Mosher
(74) Attorney, Agent, or Firm—Herbert Dubno; Jonathan Myers

(57) ABSTRACT

The invention provides new strains of the Modified Vaccinia Virus Ankara (MVA) that have a strongly reduced virulence for most mammals, especially humans, but nevertheless grows in cells of a continuous cell line approved for the production of a therapeutic agent such as a vaccine. The invention also provides a method for producing said adapted MVA strains. The adapted MVA can be used e.g. for parenteral immunization, as a vector system, or in the active or inactivated from as an adjuvant or as a regulator of the unspecific components of the immune system.

32 Claims, No Drawings

ALTERED STRAIN OF THE MODIFIED VACCINIA VIRUS ANKARA (MVA)

FIELD OF THE INVENTION

The present invention relates to new strains of the Modified Vaccinia virus Ankara (MVA) that have a strongly reduced virulence for most mammals, especially humans, but nevertheless grows in cells of a continuous cell line approved for the production of a therapeutic agent such as a vaccine. The invention also relates to a method for producing said adapted MVA strains. The MVA can be used e.g. for parenteral immunization, as a vector system, or in the active or inactivated form as an adjuvant or as a regulator of the unspecific components of the immune system.

BACKGROUND OF THE INVENTION

An organism is constantly challenged by infectious agents like bacteria, viruses, fungi or parasites. The immune system prevents the organism from permanent infection caused by these agents by the destruction and elimination of these infectious agents and any toxic molecules produced by them. The immune system can be divided into a specific and an unspecific part although both parts are closely cross linked. The unspecific immune response enables an immediate defense against a wide variety of foreign substances and infectious agents. In contrast, the specific immune response is raised after a lag phase, when the organism is challenged with a substance for the first time. However, the specific immune response is highly efficient. The specific immune response is responsible for the fact that an individual who recovers from a specific infection is protected against this specific infection but still susceptible for other infectious diseases. In general, a second infection with the same or a very similar infectious agent causes much milder symptoms or no symptoms at all. The immunity persists for a long time, in some cases even lifelong. This immunological memory is used for vaccination, where the organism is challenged with a harmless or inactivated form of the infectious agent to induce a specific immunity. Sometimes adjuvants are incorporated into vaccines to enhance the specific immune response.

Much of the knowledge about infectious diseases and immunity is contributed by studies of smallpox. The disease is caused by the variola virus, a member of the genus of Orthopox viruses. Nearly two centuries ago, prophylactic inoculations with cowpox was initiated resulting in the immunization against smallpox. Later immunization was performed with the Vaccinia virus. In the early 1950s, many of the industrialized countries had eliminated endemic smallpox by using vaccination with Vaccinia virus. However, smallpox vaccination with this Vaccinia virus resulted occasionally in serious complications, such as post-vaccinal encephalitis, generalized Vaccinia or contact infection.

A new vaccine that does not show these complications was developed by Anton Mayr. The pox vaccine consists of the pox virus Modified Vaccinia Virus Ankara (MVA) and was used for parenteral vaccination against smallpox in about 150 000 vaccinations without causing any complications related to the vaccination. Even children with immunologic deficiencies did not show serious side effects. The MVA was obtained by mutation and selection of the original vaccina virus Ankara after 575 passages in chicken embryo fibroblast cultures. The safety of this MVA is reflected by biological, chemical and physical characteristics. MVA has a reduced molecular weight, six deletions in the genome, and is highly attenuated for mammalian cells, i.e. DNA and protein is synthesized but virtually no viral particles are produced. The Modified Vaccina virus Ankara developed by Anton Mayr was deposited at the European Collection of Cell Cultures (ECACC), Salisbury, UK, under depository No. V 94012707.

The vaccination against smallpox was highly successful. In 1979, the World Health Organization declared the eradication of smallpox. Accordingly, the mass vaccination of children was discontinued and only laboratory workers and members of the armed forces of some countries are vaccinated.

With the eradication of smallpox, the predominant cause of pox infection in humans was removed. However, some non-human poxviruses have reduced host specificity, i.e. they cause infections not only in their typical host (e.g. for cowpox the cow), but also in other animals, (e.g. rats and cats). Humans can be infected by this route as well. Since parts of the population are no longer immune against smallpox, orthopox infections of animal species can be dangerous for them. Domestic animals are the main source of infection for humans. Accordingly, the vaccination of domestic animals against orthopoxviruses is of increasing importance. In addition, the MVA may be of significance as a vector for gene therapy, i.e. to transfer nucleic acid sequences into a target cell where they are expressed.

For a logarithmic reproduction of the MVA cell cultures of primary or secondary chicken embryo fibroblasts are needed. The cells are obtained from chicken eggs that are incubated for 10 to 12 days. Since eggs are subjected to a biological variability, the cells obtained for the cell culture system are variable on a cellular level as well. In addition, in a chicken embryo "fibroblast culture" often other cell types such as epithelial cells are found. This variation of the cells also results in variation of viruses produced in chicken embryo fibroblasts. It is therefore difficult to standardize and validate the cell culture system to guarantee a constantly high quality of the MVA produced. Furthermore, contamination of the cell culture system by microorganisms or viruses already present in the incubated eggs can not be completely excluded. When the MVA is grown in virus-contaminated cells, the MVA may recombine with the contaminating virus. Thereby an MVA with new and unpredictable characteristics may be generated. For the production of the virus in large scale in a suspension culture, primary or secondary chicken embryo fibroblasts are also not highly suitable. In addition, the purification and concentration of MVA by ultra gradient centrifugation would be advantageous. However, such purification is difficult, when MVA is cultivated on primary or secondary chicken embryo fibroblast. Finally, an increasing number of patients have developed allergies against chicken egg's albumen. Although the in vitro conditions of the cultivation strongly reduce the allergenic potential, a hazard of an allergic reaction can not be completely excluded.

In conclusion, on the one hand the MVA can only be efficiently grown in primary or secondary chicken embryo fibroblasts causing a number of disadvantages, however, on the other hand the save application of the MVA in humans has been shown by its large-scale application as a vaccine.

OBJECT OF THE INVENTION

It is an object of the present invention to provide conditions for the production of homogeneous virus particles of the MVA. A Additionally, said conditions should allow an easy and large-scale production of the MVA.

DETAILED DESCRIPTION OF THE INVENTION

To achieve the foregoing and other objects, the present invention provides an MVA strain that is adapted for growing in cells of a continuous cell line, said cell line being approved for the production of a therapeutic agent.

According to the present invention, for the first time an efficient and large-scale production of MVA is possible. Since cells of a continuous cell line are homogeneous and their characteristics are stable the MVA harvested from these cell lines is also homogeneous with highly predictable characteristics. Furthermore, the risk of contamination by microorganisms can be controlled and contamination of the MVA preparation by proteins of the chicken egg—as found when cultivating MVA on chicken embryo fibroblasts—can be excluded. The handling of a permanent cell line is convenient and thus highly suitable for industrial application.

In a preferred embodiment of the invention, the MVA is adapted for growing in cells of a mammalian cell line, which is approved for the production of a vaccine. It has been surprisingly found that the MVA adapted to a mammalian cell line such as the Vero cell line still has a reduced virulence for humans and also for a wide range of other mammals. Accordingly, the MVA is highly attenuated i.e. DNA and protein is synthesized but virtually no viral particles are produced, resulting in a virtually eliminated disease-causing capacity. Hence, the MVA according to the present invention is also highly suitable as a vaccine for humans and for a wide range of mammals. Accordingly, the MVA is especially applicable in the veterinary field.

Furthermore, a method to obtain an MVA strain according to the present invention is provided. According to this embodiment of the invention, cells of a cell line that is approved for the production of a therapeutic substance, are infected with the wild-type MVA. Preferably a high multiplicity of infection (MOI), i.e. a high number of viruses per cell is used for this infection. Then, the viruses are harvested and fresh cells of the same cell line are infected with the newly produced viruses. Said process is repeated (serial passaging) until the MVA is adapted to said cell line. Adaptation is reached, when 72 h post infection, the virus titer is at least 1- to 9-fold, preferably 10- to 99-fold, more preferably 100- to $10^6$-fold, and most preferably more than $10^7$- to $10^{10}$-fold increased compared to the input virus titer. The adaptation is reached after a limited number of passages.

"Adapted for growing" means that the amount of virus produced from an infection (Output) is increased compared to the amount of virus originally used to infect the cells (Input). In this case the Output/Input ratio is greater than 1.

"Derivative" of the MVA deposited at ECACC, Salisbury, UK, under the depository number 99101431 and/or provisional accession number 01021411 means an MVA which is adapted for growing in Vero cells at a rate, which is essentially the same as the growth rate of the deposited strain but carriers at least one difference in its genome compared to the deposited strain.

The term "immune system" basically describes a complex involved in the defense of the organism against foreign substances and microorganisms. It is divided into a cellular part comprising several cell types, such as e.g. lymphocytes and other cells derived from white blood cells, and a humoral part comprising peptides and proteins such as antibodies, complement factors, and cytokins.

The term "immune response" describes the reaction of the immune system, when a foreign substance or microorganism enters the organism. Generally, the immune response is divided into a specific and an unspecific reaction although both are closely cross linked. The unspecific immune response is regarded as the immediate defense against a wide variety of foreign substances and infectious agents. The specific immune response can be characterised as a highly efficient defense mechanism of the organism against a foreign substance which is raised against said substance after a lag phase and highly specific for said substance. The specific immune response is responsible for the phenomenon that an individual who has recovered from a specific infection is protected against this specific infection in future.

"Activator of the immune system" means any substance capable of provoking or enhancing an immune response.

"Suppressor of the immune system" means any substance capable of reducing or inhibiting an immune response.

"Stabilizer of the immune system" means any substance capable of keeping the immune response on a constant level.

The inventors provide two preferred MVA strains that are adapted to an African green monkey cell line, called Vero cell line (ATCC No. CCL-81). The MVA-strain, which was passaged 100-times in Vero cells was called "Vero-MVA" and deposited on Oct. 14, 1999, under the Budapest Treaty of 1977 at the European Collection of Cell Cultures Salisbury, UK under depositary No. 99101431. The MVA strain after 200 passages in Vero cells was called "Vero-MVA-200" and deposited on 14, Feb. 2001, under the Budapest Treaty of 1977 at ECACC under provisional accession number 01021411.

The MVA obtained as described above is further amplified by cultivating the cells of the approved cell line under suitable conditions, infecting cells with the MVA and harvesting the viral particles produced by said cells. Hence the MVA can efficiently and easily be amplified in large-scale. Surprisingly, the MVA of the invention does not increased virulence in cells other than Vero cells such as human cell lines including HL, HEP-2 or HeLA.

In another embodiment of the invention, the MVA contains at least one heterologous nucleic acid sequence i.e. a nucleic acid sequence that is not naturally found in the MVA genome (recombinant MVA). Preferably, the heterologous nucleic acid sequence is a gene, more preferably a gene encoding an immunizing protein, and most preferably encoding a protein immunizing against malaria, rabies and/or hepatitis. The expression of said heterologous nucleic acid sequence is preferably under the transcriptional control of a vaccinia virus promoter, more preferably of an MVA-own promoter. In a further preferred embodiment of the invention, the heterologous nucleic acid sequence is inserted at a naturally occurring deletion site in the MVA genome (disclosed in PCT/EP96/02926).

The recombinant MVA is used for the introduction of a nucleic acid sequence into a target cell, said nucleic acid sequence being homologous or heterologous to the target cell. The introduction of a heterologous nucleic acid sequence into a target cell may be used to produce heterologous nucleic acids, peptides and/or polypeptides and/or proteins encoded by said nucleic acid sequence in vitro. This method comprises the infection of a host cell with the recombinant MVA cultivation of the infected host cell under suitable conditions, and optionally isolation and/or enrichment of the peptide and/or protein produced by said host cell.

Furthermore, the introduction of a homologous or of a heterologous sequence may be applied for in vitro and preferably in vivo gene therapy. For in vitro and ex vivo gene therapy respectively, cells are isolated from the individual to be treated, transformed with the recombinant MVA and reintroduced into the individual the cells were taken from. For in vivo gene therapy, the recombinant MVA is directly administered to the living animal body including the human body. In a preferred embodiment of the invention, the recombinant MA expresses an antigen or an antigenic epitope. Most preferably, said vector expresses an antigenic determinant from Plasmodium falciparum, Mycobacteria, Herpes virus, Influenza virus, hepatitis, or a human immunodeficiency virus.

Since the MVA according to the invention is—surprisingly—still highly attenuated, the MVA is ideal to immunize a wide range of mammals including humans. Hence, the present invention also provides a vaccine comprising the MVA for the immunization of a living animal body including a human against pox infections, preferably orthopox infections. The vaccine may contain in addition to the MVA one or more additives such as an antibiotic, a preservative, or a stabilizer. The vaccine is especially applicable in the veterinary field, e.g. for the immunization of animals against orthopox infections such as cats against cat pox, mice against ectromelia or camels against camelpox. The immunization is preferably performed parenterally.

The immunizing effect of an antigenic determinant in a vaccine is often enhanced by the addition of a so-called adjuvant. An adjuvant co-stimulates the immune system in an unspecific manner causing a stronger specific immune reaction against the antigenic determinant of the vaccine. According to another embodiment of the invention, the MVA is used as an adjuvant, to co-stimulate the immune response against the antigenic determinant of a vaccine. In this case it is preferred that the MVA is inactivated. The inactivation of the MVA may be performed e.g. by heat or chemicals. Preferably, the MVA is inactivated by β-propiolacton. According to this embodiment of the invention, the inactivated MVA may be added to vaccines against numerous infectious diseases to increase the immunity against this disease.

In case of an infection, the immune, the nervous, the hormonal and the vascular system of an individual work closely together. These interactions can be regulated by elements of the unspecific immune system e.g. cytokines such as interferons and interleukins. Pox viruses can influence the regulation of the immune system (Swiss Vet 11/99, 13–17). Hence, in a further embodiment of the invention, the MVA and preferably the inactivated MVA is used in mammals including humans to regulate the cellular and humoral elements of the unspecific (innate) immune system. Preferably the MVA is used as a bioregulator, wherein dysfunctions of the immune system are eliminated and the body's own defense mechanisms are activated, stabilized and/or suppressed. Most preferably, the MVA is used as a bioregulator in case of a viral infection e.g. with herpes, hepatitis B or C virus, in case of a chronic inflammatory disease and/or to support tumor therapy. The MVA may also be used to stabilize the immune system in a situation of increased susceptibility against infections such as in the case of stress or in neonatals. The active and/or preferably the inactivated MVA can be applied systemically e.g. intramuscularly and/or locally e.g. through mucous membranes and/or skin.

In conclusion, the present invention provides MVA strains that can in general be used for the same applications as the wild-type MA, but eliminate the problems caused by the amplification of the wild-type MVA in chicken embryo fibroblasts.

SUMMARY OF THE INVENTION

The invention inter alia comprises the following, alone or in combination:

A modified vaccinia virus Ankara (MVA) adapted for growing in cells of a continuous cell line, said cell line being approved for the production of a therapeutic substance.

The MVA as above adapted for growing in cells of a mammalian cell line.

The MVA as above, wherein the cell line is approved for the production of a vaccine.

The MVA as above, wherein said approved cell line is a Vero cell line.

The MVA as above, wherein said approved cell line is the Vero cell line ATCC No. CCL-81.

The MVA as above, deposited at the European Collection of Cell Cultures, Salisbury, UK under depositary No. 99101431 and/or a derivative thereof.

The MVA as above, deposited at the ECACC, Salisbury, UK, under provisional accession number 01021411 and/or a derivative thereof.

The MVA as above, comprising at least one heterologous nucleic acid sequence.

The MVA as above comprising a heterologous nucleic acid sequence coding e.g. for a therapeutic protein and/or an antigenic determinant such as a peptide immunizing against malaria, hepatitis and/or rabies infection.

A host cell infected by the above described MVA.

A composition, preferably a pharmaceutical composition, comprising the. above described MVA and/or the DNA of the MVA.

The pharmaceutical composition described above, wherein the pharmaceutical composition is a vaccine.

The vaccine described above for the immunization of a living animal body including a human.

The vaccine as above for the immunization against an Orthopox infection.

The vaccine as above for the immunization of cats against a cat pox infection, mice against ectromelia infection and/or camels against camelpox infection.

The pharmaceutical composition described above, wherein the MVA is an activator, suppressor and/or stabilizer of the unspecific immune system.

A pharmaceutical composition comprising the above described MVA and/or the DNA of the MVA as an adjuvant.

A pharmaceutical composition comprising the above described recombinant MVA and/or the DNA of the recombinant MVA.

The pharmaceutical composition as described above for use in gene therapy.

A method for introducing a homologous and/or heterologous nucleic acid sequence into a target cell comprising infection of the target cell with the above described MVA.

A method for obtaining an WA strain as described above, comprising a) infection of cells of an approved cell line with a wild-type MVA preferably the MVA deposited at ECACC under depository No. V 94012707, b) harvesting of the viruses, c) infection of fresh cells of the same cell line with the newly produced viruses, and, optionally, d) repetition of b) and c) until the virus is adapted to growth in cells of said cell line.

A method for producing viral particles of the above described MVA, comprising cultivating the cells of an approved cell line under suitable conditions, infecting said cell line with said WA, and harvesting the viral particles produced by said cells.

The method as described above, wherein said cell line is infected with the MVA deposited at the ECACC under depositary No. 99101431 and/or the MVA deposited at the ECACC under provisional accession number 01021411 or a derivative of one of those strains.

A method for producing a nucleic acid sequence, a peptide polypeptide and/or protein, comprising infection of a host cell with the above described recombinant MVA, cultivation of the infected host cell under suitable conditions, and, optionally, isolation and/or enrichment of the nucleic acid sequence, peptide and/or protein produced by said host cell.

Use of the above described WA for producing a pharmaceutical composition for the treatment or prevention of a disease or disorder responsive to said MVA.

Use of the above described MVA for producing a vaccine for the immunization of a living animal body including a human.

Use of the above described WA for producing an activator, suppressor and/or stabilizer of the unspecific immune system.

The use as described above for the manufacture of an adjuvant.

Use of the above described MVA as a vaccine.

Use of the above described MVA as an adjuvant.

Use of the above described MVA as an activator, suppressor and/or stabilizer of the unspecific immune system.

A method for immunization of a living animal body including a human said method comprising administering to a person in need thereof a therapeutically effective amount of an above described pharmaceutical composition.

A method for introducing a homologous and/or heterologous nucleic acid sequence into a target cell comprising infecting the target cell with the above described MVA and/or the DNA of the MVA.

A method for the activation, suppression and/or stabilization of the immune system of a living animal body including a human said method comprising administration of the above described pharmaceutical composition to a living animal body including a human.

A method for enhancing a specific immune response against an antigenic determinant in a vaccine comprising administration of the above described MVA as an adjuvant to a living animal body including a human. A Modified Vaccinia virus Ankara adapted for growing in cells of a continuous cell line obtainable by a process comprising the following steps: infecting cells of a cell line being approved for the production of a therapeutic substance, harvesting the viral particles produced by said cell lines and optionally, repeating the above steps until the desired growth characteristics of said MVA are obtained in said cells.

EXAMPLES

The following examples will further illustrate the present invention. It will be well understood by a person skilled in the art that the provided examples in no way may be interpreted in a way that limits the applicability of the technology provided by the present invention to these examples.

Example 1

Adaptation of the MVA to Vero Cells and Characterization of Said MVA Strain

1. Adaptation of the MVA to Vero Cells

The by Anton Mayr developed wild-type MVA that is a modified Vaccina virus Ankara was deposited at ECACC under depository No. V 94012707. The wild-type MVA was adapted to grow in Vero-cells by serial passaging of the virus in Vero cells (Table 1). The cell clone ATCC-No. CCL-81 of the stationary Vero cell line (WHO seed stock ECACC No. 88020401) was used in the passage No. 148 to 165 (WHO seed lot, Master and Working Bank). The cells were propagated in a medium consisting of Earle's MEM (ICN), pH 7.4–7.6, and 5% of the serum substitute BMS (Biochrom). According to a technique known by people skilled in the art, always the same cells of the working bank were seeded by splitting the cells 1:2 to 1:4. The medium contained approximately 250 000 cells per ml. The cells were respectively propagated in tubes (2 ml), Roux dishes (100 ml), and plastic dishes (6 and 40 ml respectively). In general, the cells formed a confluent monolayer after 16 to 24 h. Afterwards, the medium was replaced by plain Earle's MEM without any additives.

For the adaptation of the wild-type MVA a tube culture system was used. The results of the passages are summarized in Table 1 and 2. The Vero cells were infected by 10 MOI (multiplicity of infection) of the wild-type MVA, i.e. in average, 10 viral particles per Vero cell. The wild-type MVA to start with was a genetically homogeneous, plaque-purified MVA after 575 passages in chicken embryo fibroblasts (titer: $10^{7.75}$ $KID_{50}$/ml). After 24 h, 90% of the Vero cells of the confluent monolayer were destroyed by toxic processes (50% by toxicity, 40% by lysis). The medium plus the cell dedritus after freezing and thawing of the cells, containing the produced viruses, was harvested and 0.2 ml of this mixture were seeded on the monolayer of Vero cells in the culture tubes ($2^{nd}$ passage). This procedure was repeated 200 times. After the third passage, no toxic effect was observed any more, whereas a mild cytopathic effect (CPE) characterized by rounding of the. cells and lysis in a period of 4 to 6 days post infection (p.inf.) was seen. The virus titer was $10^{1.0}$ $KID_{50}$/ml. It was concluded that the proliferation of the MVA in Vero cells had started although very inefficiently. After the fifth passage, a typical CPE was observed which was completed after 4 to 5 days p.inf. The virus titer increased from $10^{1.0}$ $KID_{50}$/ml after the third passage to $10^{4.0}$ $KID_{50}$/ml after the fifth passage. Hence, the virus amplified more efficiently in Vero cells. In the passages No. 5 to 11, a complete CPE was observed more and more early and the virus titer increased with every passage. At passage No. 11, a plateau was reached at $10^{7.5}$ $KID_{50}$/ml. Accordingly, after eleven passages the adaptation of the MVA to Vero cells was achieved. In the following 30 additional passages, the results were for all passages the same and highly reproducible: The CPE began already 24 h p.inf. and all cells were affected after three days p. inf. At that time, 20% of the Vero cells were rounded and 80% were lysed. After three days p.inf., the virus titer was always about $10^{7.5}$ $KID_{50}$/ml. After the fifteenth passage, the viruses were always harvested after two to three days p.inf., and only 1 MOI instead of 10 MOI were used to infect the cells (Table 2). In the following additional passages the growth characteristics of the MVA changed only slightly. Remarkably, the optimum virus titer further increased and reached $10^{10}$ $KID_{50}$/ml at passage 200.

In conclusion, the virus grows reproducibly in an exponential manner in Vero cells. Said growth characteristic is surprisingly different to the characteristics of the wild-type MVA Accordingly, a new strain of the MVA was obtained by the serial passaging. Said new strain was called "Vero-MVA" and after passage 200 in vero cells"Vero-MVA-200".

The Vero-MVA and Vero-MVA-200 were cultivated in larger quantities. For storage, the Vero-MVA was concentrated by centrifugation, resuspended in 2.5% polygeline and lyophilized in vials of 2 ml. The tier after lyophilization was still at least $10^{8.5}$ $KID_{50}$/ml. The lyophilized Vero-MVA and Vero-MVA-200 was checked for contamination and toxicity and stored at +4° C.

2. Characterization of the Biological Properties of the Vero-MVA

The biological characteristics of the Vero-MVA (passage 100) and Vero-MVA-200 (passage 200) were compared with the characteristics of the wild-type MVA (Table 3 and Table 5). Thereby, the techniques known by the skilled practitioner were applied. The inventors showed that neither the host range of the virus was changed except for the Vero cells, nor the virulence for humans or animals was increased. The Vero-MVA is still characterized by the abortive propagation in non-permissive host cells.

The principal identity of the viral particles of the Vero-MVA compared to the viral particles of the Elstree strain of the Vaccinia virus was shown by cross reactivity of antibodies raised against the Elstree strain. The Elstree strain is a Vaccinia strain recommended by the WHO for the smallpox vaccination. The polyclonal hyperimmune serum of rabbits raised against the Elstree strain was added to the Vero-MVA. 100 $KID_{50}$/ml of the Vero MVA were completely neutralized at a dilution of the serum of 1:512. A twofold dilution of the serum was necessary to neutralize the same amount of Vaccinia Elstree strain (1:256). Accordingly, the Vero-MVA can still be efficiently neutralized by Vaccinia immune serum.

The Vero-MVA, the Vero-MVA-200 and the wild-type MVA were compared by a number of additional tests as indicated in Table 3, 4 and 5. The inventors showed that the virulence of Vero-MVA and Vero-MVA-200 for mammals including humans was not increased compared to the wild-type MVA. It was also shown that the Vero-MVA and Vero-MVA-200 are not contagious or toxic for mammals including humans. Surprisingly, the cell specificity of the Vero-MVA was more or less identical to the specificity of the wild-type MVA except for the Vero cells: The Vero-MVA amplifies nearly as inefficiently in cells of human cell lines (see table 4: HL-, HEP-2-, and HeLa-cells) as the wild-type MVA does. Accordingly, although human cells and cells of African green monkeys are phylogenetically closely related, the Vero-MVA did not gain the ability to amplify in human cells. In other tests, no significant difference were seen either.

Furthermore, the physical, chemical, and biological characteristics of the wild-type MVA and the Vero-MVA-200 were compared (Table 5). Whereas the wild-type MVA growing in chicken embryo fibroblast cell cultures has three deletions in the left inverted terminal region, the Vero-MVA-200 has four deletions in the left terminal region compared to the genome of the pox virus as originally isolated in Ankara. Hence, passaging of the wild-type MVA in Vero cells resulted in an additional deletion.

The Vero-MVA was used to immunize domestic animals against Orthopox infections. The serum of the animals was collected and a neutralization test was performed. The inventors showed that the animals produced antibodies in high titers. The antibody titers were stable over a period of at least 111 days. It was also shown that the antibodies were able to neutralize in vitro viral particles of the MVA in a plaque-reduction test. In conclusion, the Vero-MVA can be used as a vaccine against Orthopox infections in domestic animals and in humans.

TABLE 1

Adaptation of the MVA to Vero cells

| Passage No. | Cell culture | Highest virus titer [$log_{10}$/ml] | Result | Conclusion |
|---|---|---|---|---|
| 1 | toxic effect after 24h | 2.0 | Rests of the virus seeded | Blind passages |
| 3 | No toxicity, moderate CPE after 4–6 days | 1.0 | Rests of the virus seeded? Begin of the virus reproduction | Phenomenon of zones and cytokine production |
| 5 | typical CPE completed after 4–5 days | 4.0 | Increasing virus reproduction | |
| 11 | CPE completed after 3 days | 7.5 | Logarithmic virus reproduction | Adaptation successful |
| 12–42* | CPE begins after 24h, completed after 3 days | 7.75 | Reproducible virus reproduction | Vero-MVA |

TABLE 1-continued

Adaptation of the MVA to Vero cells

| Passage No. | Cell culture | Highest virus titer [$log_{10}$/ml] | Result | Conclusion |
|---|---|---|---|---|
| 43–100* | CPE begins after 24h, completed after 3 days | 8.0 | Reproducible virus reproduction | Vero MVA |
| 100–200* | CPE begins after 24h, completed after 3 days | 10.0 | Reproducible virus reproduction | Results in Vero-MVA-200 |

*Only 1 MOI instead of 10 MOI are seeded after the eleventh passage.

TABLE 2

Change of the virus titers during the adaptation of the MVA to Vero cells

| Passage No. | Harvested after [days p. inf.] | Titer per ml [$log_{10}$/ml] |
|---|---|---|
| 1 | 1 | <2.0 |
| 2 | 3 | 2.0 |
| 3 | 5 | 1.0 |
| 5 | 5 | 4.0 |
| 8 | 4 | 6.5 |
| 11 | 3 | 7.5 |
| 18 | 2 | 8.0 |
| 19 | 2 | 7.75 |
| 20 | 3 | 8.0 |
| 25 | 2 | 7.75 |
| 29 | 2 | 7.75 |
| 30 | 3 | 7.75 |
| 31 | 3 | 8.0 |
| 45 | 2 | 7.75 |
| 51 | 3 | 7.75 |
| 60 | 2 | 8.0 |
| 66 | 2 | 7.75 |
| 68 | 2 | 8.0 |
| 75 | 3 | 8.0 |
| 100 | 2 | 8.0 |
| 200 | 2 | 10.0 |

TABLE 3

Comparison of the biological characteristics of the wild-type MVA and Vero-MVA

| Marker | Wild-type MVA | Vero-MVA (100. passage) | Vero-MVA-200 |
|---|---|---|---|
| CPE in monolayer cell cultures (1 MOI seeded) | Rounding and lysis of the cells after day 5 (90% CPE) | Rounding and lysis of the cells after day 5 (100% CPE) | Rounding and lysis of the cells after day 3 to 5 (100% CPE) |
| Titer of the optimal harvest | $10^{8.0} KID_{50}$/ml | $10^{7.75} KID_{50}$/ml | $10^{10.0} KID_{50}$/ml |
| Abortive virus reproduction in non-permissive cell systems | Yes | Yes | Yes |
| Reduced virulence for humans and animals | Yes | Yes | Yes: not virulent at all |
| Contagiousness | No | No | No |
| Character of the primary plaques on the chorion allantois membrane | No proliferative nodes without necrosis | No proliferative nodes without necrosis | No proliferative nodes without necrosis |
| Hemagglutination (chicken erythrocytes) | Negative | Negative | Negative |

TABLE 3-continued

Comparison of the biological characteristics of the wild-type MVA and Vero-MVA

| Marker | Wild-type MVA | Vero-MVA (100. passage) | Vero-MVA-200 |
|---|---|---|---|
| Inactivation by β-propiolactone | Kinetic of first order for 0.05% | Kinetic of first order for 0.05% | Kinetic of first order for 0.04–0.05% |
| Protective effect in VSV-baby-mouse challenge test | Yes | Yes | Yes |
| Toxicity for humans and animals | No | No | No |
| Cytokine stimulation | Interferon α, IL-2, and 12, CSA | Interferon α, IL-2, and 12, CSA | Interferon α and γ, IL-1, 2, and 12, CSA |
| Activation of phagocytosis, natural killer cells, and T-lymphocytes | Yes | Yes | Yes, increased |

TABLE 4

Reproduction rate in $KID_{50}$/ml of Vero-MVA and the wild-type MVA in different cell culture systems [$\log_{10}$/ml]

| Cell culture system | Vero-MVA (31.Vero-passage) | Wild-type MVA (575. passage in primary chicken embryo fibroblasts) |
|---|---|---|
| [1]) Vero (African green monkey kidney cells) | 8.0 | 4.5 |
| Primary chicken embryo fibroblasts | 4.5 | 8.5 |
| [1,2]) HL (human lung) | 3.0 | 2.5 |
| [1,2]) HEP-2 (human epidermoid carcinoma) | 3.0 | 2.5 |
| [1,2]) HeLA (human cervix carcinoma) | 2.75 | 2.75 |
| [1,2]) BHK (hamster kidney cells) | 5.75 | 5.25 |
| [1,2]) MDBK (bovine kidney cells) | 3.5 | 3.5 |
| [1,2]) PK-15 (porcine kidney cells) | 3.25 | 3.5 |

[1]) Continuous cell line derived from the tissue and species indicated in brackets.
[2]) Cell lines obtained from the collection of the institute of medical microbiology in Munich, Germany.

TABLE 5

Comparison of the wild-type MVA (572. passage in chicken embryo fibroblasts (CEF)) with Vero-MVA-200 (200. passage in vero cells)

| Marker | Wild-type MVA | Vero-MVA-200 |
|---|---|---|
| Genetic markers (comparison with pox virus strain as isolated in Ankara) | 3 deletions in the left terminal region (inverted terminal repeat) Genome size reduced from 208 to 178 kb Loss of 15% of the molecular weight of the original genome Loss of the interferon receptor | 4 deletions in the left terminal region Further reduction of the genome size to 172 kb Loss of 20% of the molecular weight of the original genome Additional loss of receptors e.g. for IL-1β |
| Cellular markers | Activation of T-helper cells (CD4, CD8, CD25) Activation of NK cells Abortive reproduction in mammalian cells (except BHK cells) | Increased activation of cytotoxic T-lymphocytes Increased activation of NK cells Further narrowing of the host spectrum in cell culture systems |
| Cytokine | Interferon α, IL-2, IL-12 | Interferon α and γ, IL-1, 2, 12 |
| Virus titer | CEF: $10^{9.5}$ $KID_{50}$/ml Vero cells: $10^{4.0}KID_{50}$/ml | CEF: $10^{4.5}KID_{50}$/ml Vero cells: $10^{9.5}KID_{50}$/ml |
| Immune system | Reduction of activity of specific immune system | Inhanced activity of the unspecific immune system |
| Virulence for humans and animals | low | none |

What is claimed is:

1. A modified vaccinia virus Ankara adapted for growing in cells of a continuous cell line, wherein said cell line is a Vero cell line.

2. The modified vaccinia virus Ankara defined in claim 1 wherein said cell line is Vero cell line ATCC No. CCL-81.

3. The modified vaccinia virus Ankara defined in claim 2 deposited at the European Collection of Cell Cultures, Salisbury, UK, under depository number 99101431 and/or a modified vaccinia virus Ankara adapted for growing in Vero cells at a rate which is the same as the growth rate of the deposited strain, but which carries at least one difference in its genome.

4. The modified vaccinia virus Ankara defined in claim 2 deposited at the European Collection of Cell Cultures, Salisbury, UK, under provisional accession number 01021411 and/or a modified vaccinia virus Ankara adapted for growing in Vero cells at a rate which is the same as the growth rate of the deposited strain, but which carries at least one difference in its genome.

5. The modified vaccinia virus Ankara defined in claim 1 comprising at least one heterologous nucleic acid sequence.

6. The modified vaccinia virus Ankara defined in claim 5 wherein the heterologous nucleic acid sequence codes for a therapeutic protein and/or an antigenic determinant.

7. A host cell infected by a modified vaccinia virus Ankara defined in claim 1.

8. A vaccine which comprises a therapeutically effective amount of the modified vaccinia virus Ankara defined in claim 1 in combination with a pharmaceutically acceptable inert carrier.

9. A vaccine which comprises a therapeutically effective amount of the recombinant modified vaccinia virus Ankara defined in claim 5 in combination with a pharmaceutically acceptable inert carrier.

10. A vaccine which comprises a therapeutically effective amount of an immunogenic pharmaceutically active ingredient together with an effective amount of the modified vaccinia virus Ankara defined in claim 1 as an adjuvant for said immunogenic pharmaceutically active ingredient in combination with a pharmaceutically acceptable inert carrier.

11. A vaccine which comprises a therapeutically effective amount of an immunogenic pharmaceutically active ingredient together with an effective amount of the modified vaccinia virus Ankara defined in claim 5 as an adjuvant for said immunogenic pharmaceutically active ingredient in combination with a pharmaceutically acceptable inert carrier.

12. A method for introducing a homologous and/or a heterologous nucleic acid sequence into a target cell, which comprises the step of infecting the target cell with the modified vaccinia virus Ankara according to claim 5.

13. A method for obtaining a modified vaccinia virus Ankara adapted for growing in cells of a continuous cell line, wherein said cell line is a Vero cell line, which comprises the steps of:
   (a) infecting cells of the Vero cell line with a wild type modified vaccinia virus Ankara to obtain modified vaccinia virus Ankara adapted to the cells of the Vero line;
   (b) harvesting newly produced modified vaccinia virus Ankara obtained from the cells of the Vero line infected according to step (a);
   (c) infecting fresh cells of the same Vero cell line with the newly produced viruses harvested according to step (b); and, optionally,
   (d) repeating steps (b) and (c) until the newly produced modified vaccinia virus Ankara is adapted to the cells of the Vero line.

14. A method for producing viral particles of a modified vaccinia virus Ankara adapted for growing in cells of a continuous cell line, wherein said cell line is a Vero cell line, which comprises the steps of:
   (a) cultivating a continuous cell line, which is a Vero cell line;
   (b) infecting said cell lines with the modified vaccinia virus Ankara; and
   (c) harvesting the viral particles produced by said cells.

15. The method for producing the viral particles defined in claim 14 wherein the modified vaccinia virus Ankara adapted for growing in cells of a continuous cell line is the virus deposited at the European Collection of Cell Cultures, Salisbury, UK, under depository number 99101431 or the virus deposited at the European Collection of Cell Cultures, Salisbury, UK, under provisional accession number 01021411, and/or a modified vaccinia virus Ankara adapted for growing in Vero cells at a rate which is the same as the growth rate of one of the deposited strains, but which carries at least one difference in its genome.

16. A method for producing a nucleic acid sequence, peptide and/or polypeptide which comprises the following steps:
   (a) infecting a host cell with the modified vaccinia virus Ankara defined in claim 5;
   (b) cultivating the infected host cell to produce the nucleic acid sequence, peptide and/or protein; and optionally
   (c) isolating and/or enriching the nucleic acid sequence, peptide and/or protein produced according to step (b) by said host cell.

17. A method of effecting an immune response in an animal subject which comprises the step of administering to said subject an effective amount of the modified vaccinia virus Ankara defined in claim 1.

18. The method of effecting an immune response defined in claim 17 wherein the immune response is a specific immune response against an Orthopox infection.

19. The method of effecting an immune response defined in claim 18 wherein the animal subject is a cat and the immune response is against cat pox.

20. The method of effecting an immune response defined in claim 18 wherein the animal subject is a camel and the immune response is against camel pox.

21. The method of effecting an immune response defined in claim 18 wherein the animal subject is a mouse and the immune response is against ectromelia infection.

22. A method for activating, suppressing or stabilizing the immune system of an animal subject which comprises the step of administering to said subject an effective amount of the modified vaccinia virus Ankara defined in claim 1.

23. A method for enhancing in an animal subject a specific immune response against an antigenic determinant in a vaccine which comprises the step of administering to said animal subject an effective amount of the modified vaccinia virus Ankara defined in claim 1.

24. A method of effecting an immune response in an animal subject which comprises the step of administering to said subject an effective amount of the modified vaccinia virus Ankara defined in claim 5.

25. The method of effecting an immune response defined in claim 24 wherein the immune response is a specific immune response against an Orthopox infection.

26. The method of effecting an immune response defined in claim 25 wherein the animal subject is a cat and the immune response is against cat pox.

27. The method of effecting an immune response defined in claim 25 wherein the animal subject is a camel and the immune response is against camel pox.

28. The method of effecting an immune response defined in claim 25 wherein the animal subject is a mouse and the immune response is against ectromelia infection.

29. A method for activating, suppressing or stabilizing the immune system of an animal subject which comprises the step of administering to said subject an effective amount of the modified vaccinia virus Ankara defined in claim 5.

30. A method for enhancing in an animal subject a specific immune response against an antigenic determinant in a vaccine which comprises the step of administering to said animal subject an effective amount of the modified vaccinia virus Ankara defined in claim 5.

31. A method of expressing a therapeutic protein in an animal subject which comprises the steps of:
   (a) isolating cells from the animal subject to be treated;
   (b) transforming the isolated cells with the modified vaccinia virus Ankara having at least one heterologous nucleic acid sequence as defined in claim 5; and
   (c) reintroducing the cells from the animal subject treated according to steps (a) and (b) back into the animal subject.

32. A method of expressing a therapeutic protein in an animal subject which comprises the step of directly administering to the animal subject the modified vaccinia virus Ankara having at least one heterologous nucleic acid sequence as defined in claim 5.

* * * * *